(12) United States Patent
Striemer

(10) Patent No.: US 10,788,437 B2
(45) Date of Patent: Sep. 29, 2020

(54) APPARATUS FOR SENSING ENVIRONMENTAL CHANGES

(71) Applicant: The Procter & Gamble Company, Cincinnati, OH (US)

(72) Inventor: Grant Edward Striemer, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/224,459

(22) Filed: Mar. 25, 2014

(65) Prior Publication Data

US 2015/0276635 A1 Oct. 1, 2015

(51) Int. Cl.
| | |
|---|---|
| *G01N 27/00* | (2006.01) |
| *G01N 27/12* | (2006.01) |
| *A61F 13/42* | (2006.01) |
| *G01D 9/00* | (2006.01) |
| *G01N 27/30* | (2006.01) |

(52) U.S. Cl.
CPC .............. *G01N 27/00* (2013.01); *A61F 13/42* (2013.01); *G01N 27/126* (2013.01); *A61F 2013/424* (2013.01); *G01D 9/005* (2013.01); *G01N 27/302* (2013.01)

(58) Field of Classification Search
CPC .. G01L 1/2293; G01N 27/041; G01N 27/127; G01N 27/126; G01N 27/04
See application file for complete search history.

(56) References Cited

U.S. PATENT DOCUMENTS

| | | | |
|---|---|---|---|
| 3,167,734 A | 1/1965 | Brucken et al. | |
| 3,983,527 A | 9/1976 | Ohsato | |
| 4,442,422 A | 4/1984 | Murata et al. | |
| 4,582,589 A | 4/1986 | Ushizawa et al. | |
| 4,621,249 A * | 11/1986 | Uchikawa | H01C 17/06586 338/34 |
| 4,717,673 A | 1/1988 | Wrighton et al. | |
| 4,942,364 A | 7/1990 | Nishijima et al. | |
| 5,679,888 A | 10/1997 | Tohda | |

(Continued)

FOREIGN PATENT DOCUMENTS

| | | |
|---|---|---|
| CN | 101382484 A | 3/2009 |
| EP | 0685736 A1 | 12/1995 |

(Continued)

OTHER PUBLICATIONS

Mu-Rong Yang et al., "Humidity sensors using polyvinyl alcohol mixed with electrolytes", Sensors and Actuators B: Chemical, vol. 49, No. 3, Jul. 1, 1998, pp. 240-247, XP055169866, ISSN: 0925-4005, DOI: 10.1016/S0925-4005 (98) 00134-8.

(Continued)

*Primary Examiner* — Son T Le
*Assistant Examiner* — Adam S Clarke
(74) *Attorney, Agent, or Firm* — Sarah M DeCristofaro; James E Oehlenschlager

(57) ABSTRACT

A sensor system comprises: a communications element and a switch configured to enable or disable the communications element. The switch comprises a switchable polymeric element. The polymeric element has at least a first electrical state and a second electrical state and is switchable between the first and second electrical states as a function of predefined environmental changes.

5 Claims, 2 Drawing Sheets

(56) References Cited

U.S. PATENT DOCUMENTS

| | | | |
|---|---|---|---|
| 5,756,879 A | 5/1998 | Yamagishi | |
| 5,841,617 A * | 11/1998 | Watkins, Jr. | H02H 5/043 |
| | | | 361/106 |
| 6,063,486 A | 5/2000 | Kobayashi | |
| 6,276,214 B1 * | 8/2001 | Kimura et al. | 73/795 |
| 6,593,588 B1 | 7/2003 | Reimer | |
| 6,902,701 B1 | 6/2005 | Hughes | |
| 7,368,312 B1 | 5/2008 | Kranz et al. | |
| 7,612,325 B1 | 11/2009 | Watkins et al. | |
| 7,972,494 B2 | 7/2011 | Tam | |
| 8,217,669 B1 * | 7/2012 | Watkins, Jr. | G01N 27/12 |
| | | | 324/693 |
| 8,482,305 B2 | 7/2013 | Johnson | |
| 2002/0149466 A1 * | 10/2002 | Sunshine | G01N 27/126 |
| | | | 338/34 |
| 2003/0020618 A1 | 1/2003 | Hemmer | |
| 2004/0217331 A1 | 11/2004 | Lussey et al. | |
| 2006/0113537 A1 | 6/2006 | Krulevitch et al. | |
| 2006/0174693 A1 | 8/2006 | Chen | |
| 2007/0114138 A1 | 5/2007 | Krasteva et al. | |
| 2007/0190327 A1 * | 8/2007 | Gartstein | A61K 8/11 |
| | | | 428/405 |
| 2008/0032049 A1 | 2/2008 | Kosowsky et al. | |
| 2009/0033467 A1 | 2/2009 | Finocchiaro et al. | |
| 2009/0212266 A1 | 8/2009 | Kosowsky et al. | |
| 2009/0278685 A1 * | 11/2009 | Potyrailo | G06K 7/0095 |
| | | | 340/572.1 |
| 2010/0073135 A1 | 3/2010 | Potyrailo et al. | |
| 2010/0090176 A1 | 4/2010 | Kosowsky et al. | |
| 2010/0156606 A1 * | 6/2010 | Gold | H04Q 9/00 |
| | | | 340/10.4 |
| 2010/0288635 A1 | 11/2010 | Komiya et al. | |
| 2011/0163850 A1 | 7/2011 | Bachman et al. | |
| 2011/0275985 A1 | 11/2011 | Lowery, Jr. | |
| 2011/0309937 A1 * | 12/2011 | Bunza | A61B 5/202 |
| | | | 340/573.5 |
| 2011/0316054 A1 | 12/2011 | Fedder et al. | |
| 2011/0320142 A1 | 12/2011 | Surman et al. | |
| 2012/0114089 A1 * | 5/2012 | Potyrailo | G21C 17/022 |
| | | | 376/247 |
| 2012/0195018 A1 * | 8/2012 | Kosowsky | 361/816 |
| 2012/0263922 A1 * | 10/2012 | Advincula | C09D 5/1681 |
| | | | 428/172 |
| 2012/0270205 A1 | 10/2012 | Patel et al. | |
| 2012/0297888 A1 | 11/2012 | Nagarajan et al. | |
| 2013/0002278 A1 * | 1/2013 | Martin | G01N 27/048 |
| | | | 324/750.3 |
| 2013/0105741 A1 | 5/2013 | Xing | |
| 2013/0162403 A1 * | 6/2013 | Striemer et al. | 340/10.1 |
| 2013/0213140 A1 | 8/2013 | Eichhorn et al. | |
| 2014/0022058 A1 | 1/2014 | Streimer et al. | |
| 2014/0083872 A1 | 3/2014 | Fuerst | |
| 2014/0105242 A1 | 4/2014 | Fernandes | |
| 2014/0318990 A1 * | 10/2014 | Star | B82Y 15/00 |
| | | | 205/787.5 |
| 2015/0068302 A1 | 3/2015 | Koo et al. | |
| 2015/0129425 A1 | 5/2015 | Tsukada et al. | |
| 2015/0276516 A1 | 10/2015 | Striemer | |
| 2015/0276643 A1 | 10/2015 | Striemer | |
| 2015/0276644 A1 | 10/2015 | Striemer | |
| 2015/0276648 A1 | 10/2015 | Striemer | |
| 2015/0276656 A1 | 10/2015 | Striemer | |

FOREIGN PATENT DOCUMENTS

| | | |
|---|---|---|
| EP | 0997730 A1 | 5/2000 |
| JP | 2006-47065 | 2/2006 |
| JP | 2007-225315 | 9/2007 |
| WO | WO 01/75429 | 10/2001 |
| WO | WO2005100965 A | 10/2005 |
| WO | WO2006125253 A | 11/2006 |
| WO | WO2010131820 A1 | 11/2010 |
| WO | WO2013101653 A1 | 1/2013 |
| WO | WO2013009875 A2 | 7/2013 |
| WO | WO 2014/043429 | 3/2014 |

OTHER PUBLICATIONS

Jun Matsui et al., "SPR Sensor Chip for Detection of Small Molecules using Molecularly Imprinted Polymer with Embedded Gold Nanoparticles", Analytical Chemistry, vol. 77, No. 13, Jul. 1, 2005, pp. 4282-4285, XP055050253, ISSN: 0003-2700, DOI: 10.1021/ac050227i.

Panda et al., "A water-soluable polythiophene-Au nanoparticle composite for pH sensing", Journal of Colloid and Interface Science, Academic Press, New York, NY vol. 316, No. 2, Sep. 20, 2007, pp. 962-967, XP022328697, ISSN: 0021-9797, DOI: 10-1016/J.JCIS.2007.08.033.

S. T. Koev et al., "Chitosan: an integrative biomaterial for lab-on-a-chip devices", vol. 10, No. 22, Nov. 1, 2010, pp. 3026-3042, XP055047231, ISSN: 1473-0197, DOI: 10.1039/c01c00047g.

International Search Report and Written Opinion, U.S. Appl. No. 14/224,441, dated Jun. 5, 2015, 10 pages.

International Search Report and Written Opinion, U.S. Appl. No. 14/224,449, dated Jun. 5, 2015, 9 pages.

International Search Report and Written Opinion, U.S. Appl. No. 14/224,459, dated Jun. 5, 2015, 10 pages.

International Search Report and Written Opinion, U.S. Appl. No. 14/224,468, dated Jun. 5, 2015, 13 pages.

International Search Report and Written Opinion, U.S. Appl. No. 14/224,475, dated Jun. 5, 2015, 12 pages.

International Search Report and Written Opinion, U.S. Appl. No. 14/224,495, dated Jun. 5, 2015, 10 pages.

U.S. Appl. No. 14/224,441, filed Mar. 25, 2014, Grant Edward Streimer.

U.S. Appl. No. 14/224,449, filed Mar. 25, 2014, Grant Edward Streimer.

U.S. Appl. No. 14/224,468, filed Mar. 25, 2014, Grant Edward Streimer.

U.S. Appl. No. 14/224,475, filed Mar. 25, 2014, Grant Edward Streimer.

U.S. Appl. No. 14/224,495, filed Mar. 25, 2014, Grant Edward Streimer.

Vaisala Humicap® Sensor for Measuring Relative Humidity (Vaisala Handbook, 2012), 2 pgs.

Lee et al., "Capacitive Humidity Sensor Tag Smart Refirgerator System using the Capacitive to Voltage Converter (CVC)", International Journal of Advanced Science and Technology, vol. 36, Nov. 2011 12 pgs.

Yuang Xiang et al., "Preparation of a novel pH-responsive silver nanoparticle/poly(HEMA-PEGMA-MAA) composite hydrogel", European Polymer Journal, vol. 43, Issue 10, 4178-4187, 2007.

Jin-Oh You et al., "Conductive, Physiologically Responsive Hydrogels", Langmuir, 26, 7, 4607-4612, 2007.

Volker Schulz et al., "In-vitro investigations of a pH- and ionic-strength-responsive polyelectrolytic hydrogel using a piezo resistive micro sensor", Proc. of SPIE, 7287, 728712, 2009.

Norman F. Sheppard Jr. et al., "Design of a conductimetric pH microsensor based on reversibly swelling hydrogels", Sensors and Actuators B, vol. 10, Issue 2, 73-77, 1993.

All Office Actions, U.S. Appl. No. 14/224,441.
All Office Actions, U.S. Appl. No. 14/224,449.
All Office Actions, U.S. Appl. No. 14/224,468.
All Office Actions, U.S. Appl. No. 14/224,475.
All Office Actions, U.S. Appl. No. 14/224,495.
Lee, et al., "RFID Coil Design", Microchip Technology, AN678, 1998, 21 pages.

* cited by examiner

1000

1000

APPARATUS FOR SENSING ENVIRONMENTAL CHANGES

FIELD OF THE INVENTION

The invention relates to sensing apparatus sensitive to environmental changes. The invention relates particularly to sensing apparatus sensitive to chemical and mechanical changes to the environment of the apparatus.

BACKGROUND OF THE INVENTION

Sensing systems are pervasive in the world today. Feedback systems with dedicated sensor and processor loops provide indications of speed, acceleration, temperature, mechanical state and a host of other pieces of information. These systems typical require expensive hardware elements to achieve their performance. There is an unmet need for sensors which may be incorporated into systems at a low cost in order to enable the provision of desired information in everyday situations for improving the daily lives of consumers. One distinct advantage of the current world in the availability of smart phones which may also serve as sensor interrogation devices via capabilities built into the device such as near field communications, RID, Bluetooth, Wife and other communications protocols which enable the devices to seek out the current state of properly configured sensors. What are needed are simple, low-cost, environmental sensors which may be remotely interrogated.

SUMMARY OF THE INVENTION

In one aspect, a sensing apparatus includes a material coating sensitive to an aspect of an environment which is subject to change. The material coating forms a portion of a sensing circuit which may be interrogated by an external system. The state of the circuit may be changed due to the response of the material coating to particularized changes to the local environment. The change in the state of the circuit may be detected by the interrogation system.

The particular environmental aspects subject to detection include the humidity level of the environment or the presence of liquid water in the environment, the presence of particular chemicals in the environment, the pH level of the environment, and the mechanical stress and accompanying strains due to mechanical changes in the environment.

DETAILED DESCRIPTION OF THE INVENTION

Figure 1:
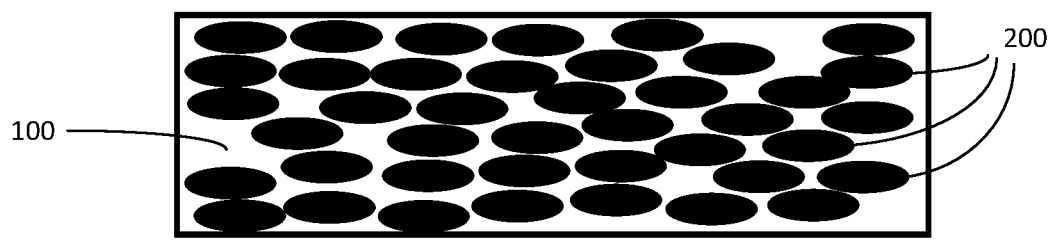
FIG. 1 provides a schematic illustration of an embodiment of the invention.

The following text sets forth a broad description of numerous different embodiments of the present invention. The description is to be construed as exemplary only and does not describe every possible embodiment since describing every possible embodiment would be impractical, if not impossible, and it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

A "chip" as described herein, may be supplanted by a chipless RFID element as is known in the art. An LC resonant RF tag, or a multiresonator element may be used in place of the chip in the described embodiments.

In one aspect, a sensor system comprises an analog-to-digital converter and sensor. The sensor is adapted to provide an output analogous to a change in pH of the environment of the sensor. The analog-to-digital converter is adapted to convert an analog output of the sensor to a digital value. The analog-to-digital value is adapted to convert an analog output of the sensor to a digital value. The analog to digital converter includes input and output terminals. The input terminals of the analog-to-digital converter are disposed in electrical communication with the output terminals of the sensor.

In one aspect, a sensor system comprises a tag. The tag may comprise one or more layers of conductive inks and non-conductive inks printed upon a substrate. Exemplary substrate materials include: polymer films, paper, high permittivity dielectric materials, and FR-4 material. Multiple layer structures may further comprise partial layers of non-conducting material separating at least portions of the conductive layers. Exemplary conductive layers include copper and silver inks. The tag comprises at least one radio-frequency chip, a first antenna disposed as a circuit upon a card, coin, or inlay. Exemplary chip/first antenna combinations include model numbers: RI-I03-112A-03 (13.56 MHz), and RI-INL-R9QM (134.2 kHz), or model TRF7970A, each available from Texas Instruments, Dallas, Tex. The antenna may be in the physical form of a coil or a dipole, or may comprise a conductive component of a product or package in electrical communication with the remainder of the tag. The chip/first antenna combination may be integrated into a unit tag available from Kovio, San Jose, Calif. The tag further comprises a conductive polymeric system in electrical communication with the chip and the antenna.

The needed power supply for the tag may be provided by the harvested energy of the RFID circuit because the needed current is in the micro ampere range. The harvested power may be stored with an element such as a capacitor for use by the tag at a later time.

In one embodiment, a sensor system comprises: a communications element and a switch. The switch may be configured to enable or disable the communications element. The switch comprises a switchable polymeric element. The polymeric element has at least a first electrical state and a second electrical state and is switchable between the first and second electrical states as a function of predefined environmental changes. The switch may enable or disable the functional capacity of the communications element of the system as or after the environmental change occurs. Exemplary environmental changes include: wetness, humidity, pH, mechanical strain, solvent compatibility, and combinations thereof.

The respective sensor elements generally function by having an electrical state which changes in response to the swelling of a sensor polymer component in response to selective changes in the environment of the sensor.

The humidity sensor may comprise a polyelectrolyte coating. When dry the polyelectrolyte smart coating has a resistance in the mega-ohms range (open circuit) and less than 3 kilo-ohms when insulted by the environment (closed circuit). When insulted by water (deionized) or humidity, the polymer swells with water thus solubilizing the electrolyte. In an un-insulted, un-swollen state, the embedded electrolyte provides an RF energy pathway to turn on the antenna enabling the RFID to transmit. In one embodiment, the smart coating formulation enables this transition at about 10 to 15 seconds after being insulted. The embedded electrolyte enhances the hygroscopic nature of this smart coating effectively making it sensitive to humidity. The wetness, pH, and mechanical strain sensor may comprise conductive filler elements enmeshed in a non-conductive polymer matrix. As the sensor is exposed to wetness or humidity, the polymer swells as it takes up water from the environment. The swelling polymer matrix reduces the conductivity of the sensor element by increasing the spacing between the discrete conductive filler particles. As this spacing increases, the pathway for conducting current through the filler of the sensor decreases and may become completely open as and after the swelling leaves no complete conductive pathway through the matrix via the filler The swelling continuum may be controlled by a pre-determined level of chemical and/or physical cross-linking. Chemical cross-linking can be induced thermally, via initiator, via UV, via photo, to name a few. Physical cross-linking can induced be from entanglements, freeze-thaw cycles, and crystallization, to name a few. The predetermined cross-linking level provides an equilibrium swell within the conductive region of the swelling region from water or humidity only. Cross-linking also serves as a way to amplify the effects of the pH sensitivity. In the cross-linked system, changes in pH cause the sensor swell or shrink in a pre-determined dynamic range.

Prior to the insult, the sensor comprises a conductive pathway comprising of a series of discrete particles of conductive material in physical contact with each other. The conductive pathway provides a path for current to flow as part of a circuit into which the sensor has been incorporated, or in an alternative, the conductive pathway may provide a known resistance as part of a circuit. As the sensor is exposed to the environmental insult, the conductivity of the sensor will fall as the swelling of the polymer matrix increases the distance between discrete conductive particles and may drop to zero in the event that the swelling creates complete separation of the conductive particles at any cross-section of the previously conductive pathway. The changes in conductivity may be correlated to environmental pH.

The chemiresistor wetness-sensitive smart coating has a resistance in the low ohms range when dry, enabling conductivity and the high mega-ohm range when insulted by the environment to cause very low conductivity. When the smart coating is insulted with water based liquid, the polymer begins to swell. This swelling induces a percolation threshold where the volume of the polymer increases to 20-40% of its dry volume. In doing so, the conductive filler reaches a point where it no longer can conduct the RF energy between the anode and the cathode side of open circuit or between two IC leads. In one embodiment, the chemiresistor smart coating formation enables this transition about 5 seconds after being insulted. To better disperse the filler, a non-ionic surfactant Triton X-100 is used.

A chemical-sensitive sensor may be created which is selective to example target chemicals with a Hildebrand solubility parameter within 2× of polyethylene co-vinyl acetate. Being insoluble in water, this system illustrates selective chemical testing in an aqueous environment. The chemiresistor in the wetness sensing was composed of a water soluble polymer: [poly(vinyl alcohol), $M_W$=89,000-98,000] and conductive filler (silver coated copper). For the chemical/biosensor, the chemiresistor's polymer can be substituted by another that has a similar solubility parameter as the target (specifically the Hildebrand Parameter).

When the selected polymer comes in contact with the analyte of interest, the polymer swells behind the conductive fillers' percolation threshold where the filler does not have sufficient contact to maintain conductivity.

The chemiresistor can be further modified to respond only to environments in a pre-determined pH range. The model polymer system may be intended for enteric coatings. Such coatings are by design made to withstand low pH in the stomach and as they pass through higher pH environments in the intestines, the polymer swells/dissolves to release medicine. In our case, for a basic pH sensor, we are interested in the system swelling past a certain pH threshold causing the filler to pass a conductive percolation threshold. This polymeric system is fundamentally an aqueous dispersion of proprietary anionic polymers functionalized with methacrylic acid. The system may be tailored to dissolve at a pH of 5.5. In one embodiment, the sensor may be configured to provide an indication of the pH of the environment. In such an embodiment, the volumetric changes of the polymer matrix according to the pH of the environment may be used to provide the indication of pH. The matrix may be configured such that there is a known volumetric change via swelling due to exposure to an aqueous environment, where the matrix responds to the environment by taking up water and swelling. The matrix may be induced to a further volumetric change by exposure to an acidic or alkaline environment relative to the $pK_a$ of the polymeric matrix. The polymer may be configured to respond to a pH increase by swelling further due to de-protonation of the acidic matrix in response to a pH in excess of the $pK_a$ of a polymeric matrix constituent component. A basic matrix may alternatively be configured to undergo protonation in response to a rising pH and undergo volumetric shrinkage.

The polymeric matrix may also be configured to respond across a range of pH values by undergoing both a volumetric shrinkage in a first part of a range and a volumetric increase in a second portion of the range. As an example, a polymeric matrix containing both acidic and basic components may be configured to shrink in volume as the environmental pH rises past the $pK_a$ of a constituent of the matrix from protonation of that acidic constituent and at a predetermined pH threshold, the basic second constituent to undergo de-protonation to cause the matrix volume to swell.

The matrix may be formulated such that it will respond to a falling pH. In one embodiment, the matrix may swell due to de-protonation as the pH of the environment falls. In an alternative, the matrix may shrink as the pH falls due to protonation of the matrix.

In one embodiment, the polymeric matrix undergoes a volumetric hysteresis associated with exposure to environmental changes of particular pH values. In such an embodiment, the polymeric matrix may undergo a volumetric change in response to a change in environmental pH and subsequently, undergo a reversal of that volumetric change in response to a reversal of the environmental pH. The hysteresis may not be completely symmetrical in that the final matrix volume at a particular pH may not precisely mirror the original state of matrix volume and pH. This incomplete hysteresis symmetry may provide an indication that an environmental event of interest has occurred as the alteration of the matrix volume of the sensor over the course of the event may yield a sensor having differing electrical characteristics than a sensor which has not undergone the insult.

In one embodiment, the polymeric matrix will transition from a first electrical state to a second electrical state when insulted by a solution having a pH in the range of interest. Subsequent to the insult the matrix may be dried yielding a third electrical state. The third state after drying corresponds to the insulted state as a function of predefined environmental pH changes, but is not electrically equivalent to the second state. Without being bound by theory, the change in electrical resistance in the third state relative to the first or second states relates to a combination of broken bonds from polymer network strain, salt retention, and re-organization of filler orientation as a function of pH and swelling.

In one embodiment, the polymeric matrix will transition from a first electrical state to a second electrical state when insulted by moisture or humidity. Subsequent to the insult, the matrix may be dried yielding a third electrical state. The third state after drying corresponds to the initial state as a function of moisture content, but is not electrically equivalent to the first state.

The polymeric strain sensor from a material standpoint is very similar to the chemiresistor. An elastic polymer is substituted for the environmental sensitive polymer. As the polymer elongates from strain, crystalline structures and physical entanglements change orientation thus changing the amount of contact of the conductive filler. As the strain increases, the conductive resistance increases. The mechanical properties, coating geometry (specifically cross-sectional area) and filler loading level influences the conductive resistance change as well as hysteresis. Ideally, the polymeric system should be insoluble to any potential chemicals that it will come in contact with. This polymeric sensor only works when the antenna configuration and attachment allows the coating to be off the tag as continuous film.

The strain sensor element may also be made directional and thereby provide an indication of the magnitude and direction of the strain upon the sensor. In one embodiment, a laminate structure is created wherein a first layer is as previously described having conductive filler particles dispersed within a polymeric matrix. A second layer may be added to this comprising only a polymeric matrix. A deformation of the laminate wherein the outer surface of the conductive layer becomes concave results in a higher conductivity as the spacing between conductive particles is reduced. Alternatively, a deformation in the opposite direction wherein the outer surface of the conductive layer becomes convex, yields greater filler particle spacing and a lower conductivity.

The tags embodying sensor and communication elements may be used to monitor an environment by following the steps of: providing a product comprising an environmentally sensitive sensor system, the sensor system comprising: a communications element and a switch configured to enable or disable the communications element, the switch comprising a switchable polymeric element, the polymeric element having at least a first electrical state and a second electrical state and being switchable between the first and second electrical states as a function of predefined environmental changes, providing an interrogator adapted to communicate with the sensor system to determine the state of the communication element, exposing the product to potential environmental changes, interrogating the state of the communications element of the sensor system. Exemplary interrogators and interrogation include the use of NFC enabled smart phones and appropriate NFC applications to query the current state of a tag placed in an environment of interest.

Figure 3:
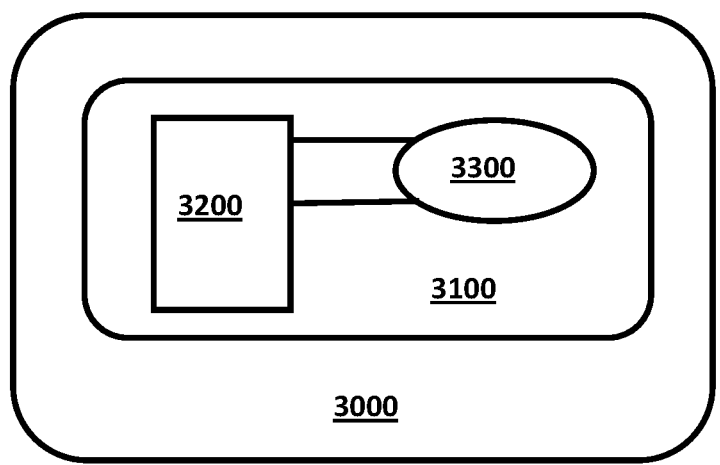
FIG. 3 provides a schematic illustration of a device according to one embodiment of the invention.

As shown in FIG. 3, the elements described herein may be configured into a device 3000 comprising a sensor system 3100. The sensor system 3100 in turn comprising: a communications element 3200 and a switch 3300 configured to enable or disable the communications element 3200. The switch 3300 comprising a switchable polymeric element, the polymeric element having at least a first electrical state and a second electrical state and being switchable between the first and second electrical states as a function of predefined environmental changes.

In one embodiment, the device may comprise a consumer product or a package for a consumer product. The sensor element may be in contact with a product within the package. The sensor may be disposed within the product in a manner and location intended to expose the sensor to a particular environmental change during the course of use of the product by the consumer. An exemplary use in this manner would include disposing a tag comprising a sensor within a diaper such that insults to the diaper while worn by an infant would produce an environmental change which in turn, would alter the electrical state of the sensor element and the tag as a whole.

Example sensor elements:

A humidity-sensitive polyelectrolyte coating with high salt content was developed as follows. A vial was filled with 10 mL of ultra-filtered deionized water. 1.1688 grams of sodium chloride was added to the vial and mixed with a magnetic stir bar at room temperature until the salt dissolved resulting in a 2 molar salt solution. When the system appeared clear, 0.3 grams of poly(vinyl alcohol) was added. The solution was heated to 90 C allowing the polymer to go into solution. When the system cleared it was ready to be applied to the surface using 10 microliter pipette tips with approximately 1-2 millimeters of the tips removed. The pipette was set to 5 microliters and the hot polymer solution was applied to the area of interest on the RFID tag. The system was then placed into a desiccant chamber and allowed to dry at room temperature overnight.

A chemiresistor wetness-sensitive polymer coating was developed as follows. A vial was filled with 9 mL of ultra-filtered deionized water. A separate vial was used to add 0.1 grams of triton X100 to 10 milliliters of ultra-filtered deionized water for a 1% by weight solution. 1 milliliter of the 1% by weight Triton X-100 was added to the 9 milliliters of ultra-filtered deionized water for a 0.1% by weight Triton X-100 solution. 0.3 grams of poly(vinyl alcohol) was added to the 0.1% by weight Triton X-100 solution, add (lower MW and higher % hydrolysis makes the system respond faster than the higher MW and lower % hydrolysis). The solution was heated to 90 C allowing the polymer to go into solution. When the system cleared, 0.1 grams of the silver coated copper (AgCU550) conductive filler, available from Ferro Electronic Materials Systems, of Mayfield Heights, Ohio, was added. The solution was sonicated (degas mode, level 5) for 5 minutes. The system was applied to the surface using 10 microliter pipette tips with approximately 1-2 millimeters of the tips removed. The pipette was set to 5 microliters and the hot polymer solution was applied to the area of interest on the RFID tag. The system was then placed into a desiccant chamber and allowed to dry at room temperature overnight.

A second chemiresistor polymer coating designed to respond not to water but instead to other environmental chemicals was developed as follows. A vial was filled with 10 mL of Trichloroethylene. 0.6 grams of [poly(ethylene co-vinyl acetate)] was added to the vial. The solution to mix at room temperature until the polymer went into solution. When the system was clear, 0.2 grams of the silver coated copper (AgCU550) conductive filler was added. The system was applied to the surface using 10 microliter pipette tips with approximately 1-2 millimeters of the tips removed. The pipette was set to 5 microliters and the hot polymer solution was applied to the area of interest on the RFID tag. The system was then placed into a fume hood and allowed to dry at room temperature overnight.

A chemiresistor polymer system designed to respond only to an environment having a pH within a target range was developed as follows: The method may use either Talc as the anti-tacking agent and triethyl citrate as the plasticizer or PlasACRYL HTP20 as the anti-tacking/plasticizer. In a 200 mL beaker, 41.7 mL of Eudragit L30 D-55, available from Evonik Industries, Essen, Germany, was added to 57 mL of deionized water, 14.6 mL of PlasACRYL HTP20, available from Evonik Industries, and 4.3 grams of the silver coated copper (AgCU550) conductive filler. The solution was mixed with a magnetic stir bar for 10 minutes. The solution was used to coat the desired area of the RF tags and cured in a circulating drying oven for 2 hours at 40 C. The RFID tag turned off when the polymer was exposed to an environment having pH values greater than 5.5.

Additional chemiresistor sensor systems have been designed to respond to an environmental change in pH. It is understood, without being limiting, that polymers, initiators and/or cross-linkers suitable to form a pH sensitive matrix in combination with conductive filler could include or be a combination of: poly(acrylic acid) (PAA), acrylic acid (AA), 2-hydroxyethyl methacrylate (HEMA), poly(hydroxyethyl methacrylate-co-methacrylic acid) (PHEMA-co-MAA), poly(acrylic acid-co-isooctyl acrylate) (poly(AA-co-IOA), poly(acrylamide) (PAAm), poly(methacrylic acid) (PMAA), poly(diethylaminoethyl methacrylate) (PDEAEMA), poly(dimethylaminoethyl methacrylate) (PDMAEMA), poly(vinyl alcohol) (PVOH or PVA), poly(ethylene glycol)dimethacrylate (PEGDMA), acrylamide (AAm), N,N-dimethylaminoethyl methacrylate (DMAEMA), N-isopropylacrylamide (NIPAAm), 2-(dimethyl maleinimido)acrylamide (DMIAAm), 2-(dimethyl maleinimido)ethyl methacrylate (DMIMA), poly(2-vinylpyridine) (P2VP), poly(4-vinylpyridine) (P4VP), ethylene glycol dimethacrylate (EGDMA), glutaraldehyde, azobiz-methylpropionitrile (AIBN), glyoxal, glycerol, cellulose families, any polymer or molecule with alcohol functional groups, any polymer or molecule with carboxylic acid functional groups.

The model conductive composite system is composed conductive graphitized carbon as the conductive filler and a polymer matrix composed of poly(vinyl alcohol) and poly (acrylic acid). It is understood that a cross-linked water-sensitive polymer could be composed of any previously mentioned polymers but not necessarily sensitive to pH.

Sensing materials may be prepared as follows:

PVOH/PAA/Filler Composite Sensor Element:

Fill two, 150 mL Pyrex glass beakers with 40 mL of deionized water. Add a magnetic stir bar and place beakers on hot/stir plates. Set the stirrers to 400 rpms. Weigh out 3 grams of A99 conductive, graphitized, carbon filler (44 micron diameter) available from Asbury Carbon, and add to each beaker. Allow the stirrer to mix the dry powder into solution. Manually mixing with a spatula can help push any residual powder into solution. Remove the beakers from hot/stir plates and place in a sonication bath and sonicate for 5 minutes to better disperse the filler. After sonication, place the beakers back onto the hot/stir plates. Set the temperature of the polyvinyl alcohol (PVOH) and poly(acrylic acid) (PAA) hot/stir plates to 200 C with stirrers set to 400 rpms. Weigh out 4 g of PVOH (89-98K MW, 99% hydrolyzed) and 4 g of PAA (450K MW), available from Sigma Aldrich, into weigh boats. The PVOH can be added to the beaker all at once. The PAA needs to be slowly added to prevent clumping in solution. After each spatula added, enough time is allowed for the polymer powder on the surface to go into solution before adding the next spatula. Once the polymers are sufficiently dispersed in solution, JKEM thermocouples are added to monitor the temperature to ensure they stay between 70-80 C. The systems are covered with paraffin film and allowed to dissolve for three hours. After three hours, the heat is turned off and systems are allowed to cool for 30 minutes while still being stirred. When the temperature falls below 30 C, combine PVOH and PAA solutions into a 500 mL beaker. An overhead mechanical mixer is used to handle the higher viscosity and to prevent bubble formation. The two solutions are mixed at room temperature for at least two hours at 70 rpms but preferably as long as 17 hours control viscosity and prevent filler settling. After mixing, remove any surface bubbles with a disposable pipette. Pour the resultant solution into a 150×20 mm Petri dish and allow to dry overnight. Alternatively, pour the resultant solution into a syringe to inject over conductive leads to form sensors. After air drying, use a razor blade to trace around the edge of the Petri dish or drying surface and carefully remove to prevent plastically straining of the polymeric system. Place between two silicone sheets and cure at 130 C for 1 hour. It is understood that alternative cure times and temperatures can be used to achieve esterification between the carboxylic acid groups on the PAA and alcohol groups on the PVOH. Remove and allow cooling to room temperature before separating the silicone sheets.

PAA/Glycerol/Filler Composite Sensor Element:

Fill a 150 mL Pyrex glass beaker with 80 mL of deionized water. Add a magnetic stir bar and place beaker on a hot/stir plate. Set the stirrer to 400 rpms. Weigh out 2.4 grams of A99 conductive, graphitized, carbon filler (44 micron diameter) available from Asbury Carbon, and add to the beaker. Allow the stirrer to mix the dry powder into solution. Manually mixing with a spatula can help push any residual powder into solution. Remove the beaker from hot/stir plates and place in a sonication bath and sonicate for 5 minutes to better disperse the filler. After sonication, place the beaker back onto the hot/stir plate. Set the temperature of the hot/stir plate to 200 C and stirrer to 400 rpms. Weigh out 8 g of PAA (450K MW), available from Sigma Aldrich, into a weigh boat. The PAA needs to be slowly added to prevent clumping in solution. After each spatula added, enough time is allowed for the polymer powder on the surface to go into solution before adding the next spatula. Once the polymers are sufficiently dispersed in solution, a JKEM thermocouple is added to monitor the temperature to ensure it stays between 50-60 C and allow the system to dissolve for three hours while covered with paraffin film. After three hours, the heat is turned off the stir plate is allowed to cool. After the solution's temperature falls below 30 C, remove from the hotplate to an overhead mechanical mixer. An overhead mechanical mixer is used to handle the higher viscosity and to prevent bubble formation. Slowly add 0.8 g of glycerol, available from Sigma Aldrich. The two solutions are mixed at room temperature for 1 hour at 70 rpms. After mixing, remove any surface bubbles with a disposable pipette. Pour the resultant solution into a 150×20 mm Petri dish and allow to dry overnight. The polymeric system may also be incorporated into a mold with conductive leads. After air drying, use a razor blade to trace around the edge of the Petri dish and carefully remove to prevent plastically straining of the composite. Place between two silicone sheets and cure at 130 C for 1 hour. It is understood that alternative cure times and temperatures can be used to achieve esterification between the carboxylic acid groups on the PAA and alcohol groups on glycerol. Remove and allow cooling to room temperature before separating the silicone sheets.

PAA/Filler Composite Sensor Element:

Fill a 150 mL Pyrex glass beaker with 80 mL of deionized water. Add a magnetic stir bar and place beaker on a hot/stir plate. Set the stirrer to 400 rpms. Weigh out 2.4 grams of A99 conductive, graphitized, carbon filler (44 micron diameter) available from Asbury Carbon and add to the beaker. Allow the stirrer to mix the dry powder into solution. Manually mixing with a spatula can help push any residual powder into solution. Remove the beaker from hot/stir plates and place in a sonication bath and sonicate for 5 minutes to better disperse the filler. After sonication, place the beaker back onto the hot/stir plate. Set the temperature of the hot/stir plate to 200 C and stirrer to 400 rpms. Weigh out 8 g of PAA (450K MW), available from Sigma Aldrich, into a weigh boat. The PAA needs to be slowly added to prevent clumping in solution. After each spatula added, enough time is allowed for the polymer powder on the surface to go into solution before adding the next spatula. Once the polymer is sufficiently dispersed in solution, a JKEM thermocouple is added to monitor the temperature to ensure it stays between 50-60 C and allow the system to dissolve for three hours and until covered with paraffin film. The heat is turned off and the stir plate is allowed to cool for 30 minutes. After mixing, remove any surface bubbles with a disposable pipette. Pour the resultant solution into a 150×20 mm Petri dish and allow to dry overnight. The polymeric system may also be incorporated into a mold with conductive leads. After air drying, use a razor blade to trace around the edge of the Petri dish and carefully remove to prevent plastically straining of the composite. Place between two silicone sheets and cure at 130 C for 1 hour. It is understood that alternative cure times and temperatures can be used to achieve self-crosslinking between the carboxylic acid groups on the PAA to form acid anhydrides. Remove and allow cooling to room temperature before separating the silicone sheets.

Material Preparation:

To dissolve the polymer into an aqueous solution, heat is added to the system. The polymers are dissolved in separate beakers and combined later to ensure phase separation between the polymer systems does not occur during the drying process. Even though hydrogen bonding readily occurs between the carboxylic acid of the PAA and alcohol of either PVOH or glycerol, above 62 C free volume effects dominate. To circumvent this, the respective polymer solutions are allowed to cool to room temperature while mixing in their respective beakers. Once at room temperature, the PAA is added slowly to the crosslinking system (PVOH or glycerol) and allowed to mix for two hours to ensure the two systems are well dispersed for hydrogen bonding. Longer mixing is done to remove water from the system to increase viscosity to prevent filler from settling during the drying process. In practice, the phase separation was identified with ATR spectra as well as anomalies in the pH sensing data. A mechanical stirrer is used in the final step to avoid creating air bubbles in the polymer system.

The pH sensor cross-linking was validated by ATR spectra for ester formation using a Thermo Nicolet Nexus 670 FTIR and several day exposures to aqueous systems to verify that the system does not dissolve. To acquire dynamic resistance data from the sensor and prevent electrolysis, a power source supplied 1.0 volts and the resultant current was measured by 2831E Measurement (Data Logging Multimeter). Initially, alligator clips were used to attach to the sensing material. The measured current was converted to resistance using Ohm's law. Later improvements were made where copper wires were cured into the sensing material to improve measurements and scalability. The weight of the sensor was also recorded to keep track changes as a function of pH.

The pH sensors were tested for dynamic readings while in solution. In pH's 3 and 10, a swelling plateau was reached around 2 minutes with corresponding resistance changes for the PAA/PVOH version. In pH's 3 and 10, a swelling plateau was reached around 1 minute 30 seconds with corresponding resistance changes for the PAA/Glycerin version. Because PAA can be readily de-protonated and protonated as a function of pH and time, a proof-of-concept hysteresis loop test was conducted using a single sensor with the leading PAA/PVOH system. A weight was recorded for the sensor before the initial insult starting at pH 4. One hour subsequent insults and weight changes from de-protonation were recorded for pH's 5, 5.5, 6, 7, and 9. In an ideal system, the reversing of the same pH insults would cause the new volume to shrink back to the respective volumes. However, volume shrinkage undergoes hysteresis due to protonating time constants, pH distance from the pKa value, irreversible changes to the strain network from some broken acid anhydride and PAA/PVOH ester bonds create a hysteresis. This hysteresis can be correlated to insult time and environmental pH and ultimately an electrical resistance value. Once the pH falls to the pKa of the polymer, the protonation will plateau.

A polymeric system sensitive to mechanical strain was developed by substituting an elastic polymer for the environmentally sensitive polymer as follows: 8 grams of silicone RTV rubber was mixed with 8 grams of conductive filler in a beaker to obtain a 50/50 ratio of polymer. The mixture was extruded through a plastic 20 mL syringe. The strips were extruded onto a silicone surface for easy removal. In one embodiment, an additional layer of the silicone was extruded upon the silicone conductive filler layer and allowed to cure. The room temperature vulcanization was allowed to proceed for 24 hours. The strain sensor strip was removed and tested for dynamic conductivity and mechanical properties (Young's modulus, elastic region, Yield point). The Instron was set to constant extension at 1 mm/sec until break. The resistance was measured in parallel with a 2831E Measurement (Data Logging Multimeter) and small alligator clips attached to the sample. The Young's modulus was calculated with the Instron software. A secondary test was conducted without alligator clips where the final strain of 150% strain from extension where the break occurred in the middle of the strain sensor.

The exemplary tag systems demonstrate the incorporation of the sensor elements and the communication elements. The sensor elements may also be created as standalone devices for use in any system where an electrically switchable sensor for the described environmental changes is desired.

A polymeric system sensitive to directional strain was developed by tailoring the viscosity of a polymer system such that filler will settle with gravity to result in a predetermined non-conductive to conductive continuum in the matrix. With this filler loading level continuum, directional strain may be identified with a drop in resistance as the system is bent toward the conductive side or an increase in resistance as it is bent toward the non-conductive side. The polymer system may be thermoset, thermoplastic, or elastomer in nature. Suitable polymer families are esters, amides, urethanes, silicones, epoxy resins, ethers, ethylene, and vinyl to name a few. Conductive filler can be metallic or non-metallic. In our case, a model system was designed with non-metallic, conductive graphitized carbon filler and a polymer matrix composed of poly(vinyl alcohol) and poly(acrylic acid).

PAA/PVOH/Filler Directional Strain Sensor Composite:

Fill two, 150 mL Pyrex glass beakers with 40 mL of deionized water. Add a magnetic stir bar and place beakers on hot/stir plates. Set the stirrers to 400 rpms. Weigh out 1.2 grams of A99 conductive, graphitized, carbon filler (44 micron diameter) available from Asbury Carbon, and add to each beaker. Allow the stirrer to mix the dry powder into solution. Manually mixing with a spatula can help push any residual powder into solution. Remove the beakers from hot/stir plates and place in a sonication bath and sonicate for 5 minutes to better disperse the filler. After sonication, place the beakers back onto the hot/stir plates. Set the temperature of the polyvinyl alcohol (PVOH) and poly(acrylic acid) (PAA) hot/stir plates to 200 C with stirrers set to 400 rpms. Weigh out 4 g of PVOH (89-98K MW, 99% hydrolyzed) and 4 g of PAA (450K MW), available from Sigma Aldrich, into weigh boats. The PVOH can be added to the beaker all at once. The PAA needs to be slowly added to prevent clumping in solution. After each spatula added, enough time is allowed for the polymer powder on the surface to go into solution before adding the next spatula. Once the polymers are sufficiently dispersed in solution, JKEM thermocouples are added to monitor the temperature to ensure they stay between 70-80 C. The systems are covered with paraffin film and allowed to dissolve for three hours. After three hours, the heat is turned off and systems are allowed to cool for 30 minutes while still being stirred. When the temperature falls below 30 C, combine PVOH and PAA solutions into a 500 mL beaker. An overhead mechanical mixer is used to handle the higher viscosity and to prevent bubble formation. The two solutions are mixed at room temperature for at least two hours at 70 to mix thoroughly but maintain water content for low viscosity to enable the filler to settle into a continuum. After mixing, remove any surface bubbles with a disposable pipette. Pour the resultant solution into a 150×20 mm Petri dish and allow to dry overnight. After air drying, use a razor blade to trace around the edge of the Petri dish or drying surface and carefully remove to prevent plastically straining of the polymeric system. Place between two silicone sheets and cure at 130 C for 1 hour. It is understood that alternative cure times and temperatures can be used to achieve esterification between the carboxylic acid groups on the PAA and alcohol groups on the PVOH. Remove and allow cooling to room temperature before separating the silicone sheets.

Strips of material were cut in 1 cm by 4 cm strips and clamped with alligator clips at the ends. A fluke multimeter was used to acquire resistance changes. The equilibrium resistance was about 490 ohms. As the sensor was bent toward the conductive side, the resistance lowered to 336 ohms due to compression of conductive filler. As the sensor was bent toward the non-conductive side, the resistance increased to 618 ohms due to slipping and separation of conductive filler pathways. After releasing the strain, the sensor returned back to its equilibrium value of about 490 ohms.

Figure 2:
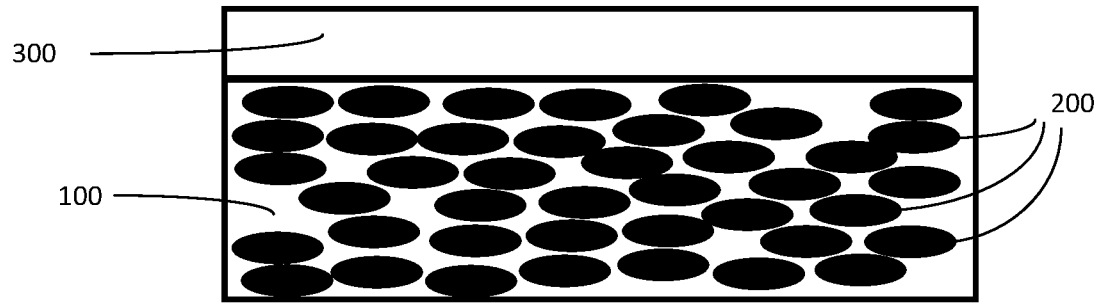
FIG. 2 provides a schematic illustration of an embodiment of the invention.

As shown in FIG. 1, a sensor element 1000 includes a polymeric matrix 100 and conductive filler elements 200, embedded in the matrix. As shown in FIG. 2, the sensor element 1000 comprises a polymeric matrix 100, conductive filler 200 and a layer of unfilled matrix 300.

In one aspect, the sensor system comprises a tag. The tag may comprise one or more layers of conductive inks and non-conductive inks printed upon a substrate. Exemplary substrate materials include: polymer films, paper, high permittivity dielectric materials, and FR-4 material. Multiple layer structures may further comprise partial layers of non-conducting material separating at least portions of the conductive layers. Exemplary conductive layers include copper and silver inks. The tag comprises at least one sensor, a radio-frequency chip, and a first antenna disposed as a circuit upon a card, coin, or inlay. The chip may be active or passive. Exemplary chip/first antenna combinations include model numbers: RI-I03-112A-03 (13.56 MHz), and RI-INL-R9QM (134.2 kHz), or model TRF7970A, each available from Texas Instruments, Dallas, Tex. The antenna may be in the physical form of a coil or a dipole, or a conductive component of a product or package in electrical communication with the remainder of the tag.

The needed power supply for the sensors may be provided by the harvested energy of the RFID circuit because the needed current is in the micro ampere range. The harvested power may be stored with an element such as a capacitor for use by the sensor at a later time.

The tag may be configured such that the output of the sensor alters the value of one or more bits of the word stored in the memory of the tag's chip. In one embodiment, any non-zero sensor output may alter a designated bit's value either from one to zero or from zero to one. Alternatively, the tag's circuit may provide a bias against which the sensor output is compared. In this embodiment, only sensor outputs above the bias threshold, or between a lower and upper set of thresholds may alter the bit's value.

The tag may comprise more than a single sensor. In one configuration of a multi sensor tag, each sensor's output may be used to alter the value of its own respective bit. In an alternative configuration, the set of sensors may be polled when the tag is powered such that a single particular bit of the tag's memory is stepped through a series of values depending upon the output of each polled sensor. As noted before, the tag may be designed such that any non-zero sensor output will alter the value of the associated bit, or such that only values above a lower threshold, or between an upper and lower threshold will alter the respective bit value.

The tag may be read using a radio frequency protocol such as the Near Field Communications (NFC) protocol. When the tag is interrogated, or read, the tag circuit is powered, the sensor output alters the memory of the tag. The memory of the tag is then read by an interrogator. The interrogator acquires a digital value of the memory word indicative of the sensed state of the environment of the tag. The relevant communications frequency range of the tag may be HF, UHF or other appropriately selected frequency ranges as determined by the specific need of the tag in terms of the intended environment and uses of the tag.

The sensor system may further comprise an interrogator. The interrogator comprising a power source and a second antenna adapted to generate electromagnetic radiation comprising a resonant frequency of the first antenna, and a receiver adapted to detect electromagnetic radiation and de-modulate the detected radiation extracting embedded data from the detected radiation. The Bluetooth™ RFID Reader, model number 223012, available GAO RFID, of Toronto Canada, exemplifies one form of interrogator. The model 223012 interrogator has the capacity to interrogate the radio frequency tag and to determine the state of the memory of the tag and thus extract information associated with the output of the sensor or sensors relating to the environment of the tag. The 223012 further comprises a secondary network communications link utilizing the Bluetooth™ communications protocol for transmitting the information extracted from the tag to a secondary device or secondary interrogator, such as a Bluetooth™ enabled computer or smart phone. The secondary interrogator may further analyze the information relating to the state of the tag and/or the tags environment and provide an output associated with a particular tag and/or tag environment state. The interrogator may further comprise a display element such as an LCD or LED screen for displaying an output associated with the analyzed tag information. The interrogator may further comprise one or more sensors for ascertaining information associated with the environment of the interrogator. The sensors may include: temperature, humidity, acceleration sensors. The interrogator may further comprise one or more cameras enabling the capture of images associated with a product, the tag or the environment. The interrogator may comprise a Global Positioning capability enabling the interrogator to ascertain and share information relating to the geographic location of the interrogator.

In one aspect, the Smartphone may serve as the only interrogator. In this aspect the smart phone may interrogate the tag thereby ascertaining the information from the memory of the tag. The interrogator may analyze or otherwise interpret the information and may create an output. The output may be provided to a system user via an audio output, visual output, haptic output or combinations thereof. The interrogator may utilize inputs from sensors or systems of the smart phone, including information and analysis available from a networked resource such as cloud computing resources, in addition to the tag information in creating the output. Exemplary smart phones suitably configured to perform as a system interrogator include: the Acer™ E320 Liquid Express, the Blackberry™ Bold™ 970, available from Research In Motion of Waterloo, Ontario, Canada; the Casio IT-800; the Google Nexus 7™, available from Google, Inc. Mountain View Calif.; the HTC Desire C™; the LG Optimus Elite; the Motorola Droid™ Razr™; the Nokia 700; the Panasonic BizPad™; and the Samsung Galaxy S Advance™.

In one aspect, the sensor system may include a product. The term "product(s)" is used in the broadest sense and refers to any product, product group, services, communications, entertainment, environments, organizations, systems, tools, and the like. For example, an example of a product group is personal and household products, such as used by a person, family or household. Examples of a representative, and non-limiting list of product categories within the personal and household product group includes antiperspirants, baby care, colognes, commercial products (including wholesale, industrial, and commercial market analogs to consumer-oriented consumer products), cosmetics, deodorants, dish care, feminine protection, hair care, hair color, health care, household cleaners, laundry, oral care, paper products, personal cleansing, disposable absorbent articles, pet health and nutrition, prescription drugs, prestige fragrances, skin care, foods, snacks and beverages, special fabric care, shaving and other hair growth management products, small appliances, devices and batteries, services such as haircutting, beauty treatment, spa treatment, medical, dental, vision services, entertainment venues such as theaters, stadiums, as well as entertainment services such as film or movie shows, plays and sporting events A variety of product forms may fall within each of these product categories.

Exemplary product forms and brands are described on The Procter & Gamble Company's website www.pg.com, and the linked sites found thereon. It is to be understood that consumer products that are part of product categories other than those listed above are also contemplated by the present invention, and that alternative product forms and brands other than those disclosed on the above-identified website are also encompassed by the present invention.

Other product groups include but are not limited to: sports equipment, entertainment (books, movies, music, etc), vision, and in-home-consumed medical and first aid, among others.

The tag may be attached to the packaging of the product such as the primary packaging of a liquid product, or a granular product. The tag may be immersed in or float upon the surface of a packaged liquid or granular product. The tag may be incorporated within the product such as within a disposable absorbent article such as within a diaper for the purpose of detecting an insult to the absorbent core of the diaper. The tag may be disposed upon the surface of the product itself such as upon the surface of a battery for the purpose of sensing information relating to the useful power remaining in the battery.

It is believed that conforming the antenna of the tag to the shape of the outer surface of the product yields a system where communication between the interrogator and the tag may be omni-directional or achievable at a variety of angles between the interrogator and the tag.

One of the problems associated with creating a communication device for various products is realized when the communication device is utilized on electromagnetically conductive bodies. Free space radio propagation principles do not apply near highly conductive bodies. Additionally, antenna performance is severely degraded when antennas are placed near metals. As such, simply placing an RFID tag on a battery or on an object with a conductive body may not accomplish the desired effect, e.g. power harvesting and/or data transfer. Notably, this problem is not limited to rechargeable/disposable batteries. For example, a can of shaving gel, foam, etc., or a package comprising a metallized film, could experience the same issues because of the conductivity of the container. In general, an RFID tag next to metallic body decreases signal coupling between the reader and the tag by 10×.

One way to prevent the effects arising from metal proximity to the antenna is to prevent the electromagnetic field from entering the metal. For example, separating the antenna and the metal surface by placing a material with suitable electromagnetic properties and dimensions between them may divert the electromagnetic field around the metallic/conductive body of the product. The properties of the diverter material depend on the exact metal used and the RFID frequency. The magnetic diverter effectively isolates the tag from the can. An effective separation may also be achieved with an air filled gap between the materials.

In one aspect, a method of determining product information comprises steps of: providing a product comprising a tag as described above. The tag comprising, at least one sensor adapted to provide an output analogous to a change in an environment of the sensor. The sensor having at least one output terminal. The tag also includes a radio-frequency chip comprising a memory element, input terminal(s) and output terminal(s), the input terminal(s) disposed in electrical communication with the output terminals of the sensor, and a first antenna disposed in electrical communication with the output terminals of the chip.

The method may also include providing an interrogator adapted to detect radiation associated with the data of the tag. The interrogator may be an RF or NFC protocol reader coupled with a Bluetooth™ capability as described above, or a smart phone or other computing device comprising an RF or NFC capable reader.

In one aspect the method may be minimized to providing products including tags and providing software compatible with devices available in the market or in the possession of consumers. A consumer may choose to avail themselves of the application software which will enable their device to functions as the described interrogator.

The interrogator may be used to determine the current state of the tag utilizing an RF communications protocol such as the NFC protocol. The interrogator may interpret the data received from the tag using a software application written for that purpose.

In one aspect, the interrogator may incorporate a secondary network communication module affording the device an ability to send and receive data over a cellular phone or other networks including a local area or WIFI networks. In such an aspect, the interrogator may transmit data received from the tag and/or an analysis of the data from the tag. The software application of the interrogator may analyze the data from the tag to determine if replenishment of the product associated with the tag in needed, or to project when such replenishment will be needed in view of usage history of the product established via a series of interrogations of the tag. In this aspect the application may be used to consummate a purchase of addition product via the network. The application may be further utilized to offer the user related products for purchase, or to make offers of other products not directly related to the product.

In one embodiment, the system tag may be subdivided into portions. One portion may contain the antenna and the chip, the other portion may contain the sensor. The two portions of the tag may be disposed with the sensor exposed to the functional environment of an absorbent article, and the antenna and chip portion removed from exposure to the functional environment of the article. The antenna and chip portion may be made removable and therefore reusable as well. In one embodiment, conductive hook and loop fasteners, such as are available from APLIX Inc., of Charlotte, N.C., may be used to create an interface between the functional environment of the article and the exterior of the article. The attachment mechanism between the article, sensor and the removable tag to enable conductivity can be hook & loop, compression (e.g. elastic band, garter), adhesion (e.g. adhesive strip), magnetic, or combinations thereof. In this embodiment, the sensor may be fabricated as an assembly in electrical contact with the conductive hook and loop pads which in turn are disposed upon an exterior surface of the article while the sensor may be disposed within the article in the functional environment. Matching pads may be incorporated as part of the assembly of the antenna and chip assembly and the two respective assemblies may be united using the matching hook and loop pads for operational use of the tag. In this manner, the more costly antenna and chip assembly may be rendered reusable thereby reducing the overall cost associated with using the system with a number of respective disposable articles. The respective assemblies may be formed using conductive adhesive, such as is available from MG Chemicals, of Surrey, B.C., Canada to affix the electrical leads of the respective portions of the tags to their respective hook and loop fastener pads.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sensor system comprising:
   a communications element comprising a tag, wherein the tag comprises an antenna and a chip; and
   a switch configured to alter a value of one or more bits stored in a memory of the chip, the switch comprising a switchable polymeric element, the polymeric element having a first electrical state and a second electrical state and being switchable between the first and second electrical states as a function of predefined environmental changes, wherein the predefined environmental change is selected from the group consisting of: wetness, humidity, pH, mechanical stress, solvent compatibility, and combinations thereof; wherein the polymeric element comprises a non-conductive polymer matrix and discrete conductive filler particles enmeshed in the non-conductive polymer matrix, wherein the discrete conductive filler particles comprise particles selected from the group consisting of graphitized carbon powder and silver coated copper powder, and wherein the polymeric element undergoes a volumetric change between the first electrical state and the second electrical state, wherein the first electrical state corresponds to a first one or more bits and the second electrical state corresponds a second to one or more bits, wherein the first one or more bits of the first electrical state are different than the second one or more bits of the second electrical state; and wherein the tag is configured to be read by an interrogator, wherein the interrogator reads the tag and the first one or more bits of the first electrical state or the second one or more bits of the second electrical state when the tag is powered.

2. A method of monitoring an environment, the method comprising:

providing a product comprising an environmentally sensitive sensor system, the sensor system comprising:
a communications element comprising a tag, wherein the tag comprises a radio-frequency chip and a first antenna, and wherein the chip comprises a memory; and
a switch configured to alter a value of one or more bits stored in a memory of the chip, the switch comprising a switchable polymeric element, the polymeric element having a first electrical state and a second electrical state and being switchable between the first and second electrical states as a function of predefined environmental changes wherein the predefined environmental change is selected from the group consisting of: wetness, humidity, pH, mechanical stress, solvent compatibility, and combinations thereof, wherein the polymeric element comprises a non-conductive polymer matrix and discrete conductive filler particles enmeshed in the non-conductive polymer matrix, wherein the discrete conductive filler particles comprise particles selected from the group consisting of graphitized carbon powder and silver coated copper powder, wherein the first electrical state corresponds to a first one or more bits and the second electrical state corresponds a second to one or more bits, wherein the first one or more bits of the first electrical state are different than the second one or more bits of the second electrical state;

providing an interrogator adapted to communicate with the sensor system to determine the state of the communication element, wherein the interrogator comprises a second antenna;

exposing the product to the environmental change;

changing a volume of the polymeric element between at least one of the first electrical state and the second electrical state;

altering of one or bits in the memory of the tag based on the change from the first electrical state to the second electrical state; and interrogating of the communications element of the sensor system using the interrogator, wherein the second antenna of the interrogator communicates with the first antenna of the tag, and wherein the interrogator determines a state of the memory of the tag.

3. A device comprising a sensor system, the sensor system comprising:
a communications element comprising a tag, wherein the tag comprises a chip having a memory, wherein the memory is configured to store or more bits; and
a switch configured to alter a value of one or more bits stored in a memory of the chip, the switch comprising a switchable polymeric element, the polymeric element having at least a first electrical state and a second electrical state and being switchable between the first and second electrical states as a function of predefined environmental changes, wherein the predefined environmental change is selected from the group consisting of: wetness, humidity, pH, mechanical stress, solvent compatibility, and combinations thereof; wherein the polymeric element comprises a non-conductive polymer matrix and discrete conductive filler particles enmeshed in the non-conductive polymer matrix, wherein the discrete conductive filler particles comprise particles selected from the group consisting of graphitized carbon powder and silver coated copper powder, and wherein the polymeric element undergoes at least one volumetric change in response to the predefined environmental change;
wherein the one or more bits stored in the memory of the chip is altered based on the change between the first electrical state and the second electrical state, and
wherein the memory of the tag is configured to be read using a radio frequency protocol.

4. A sensor system comprising:
a communications element comprising a tag, wherein the tag comprises a sensor, a radio-frequency chip, and a first antenna, wherein the sensor is configured to generate a sensor output, and wherein the radio-frequency chip comprises a memory; and
a switch configured to alter the sensor output, the switch comprising a switchable polymeric element, the polymeric element having at least a first electrical state and a second electrical state state and being switchable between the first and second electrical states as a function of predefined environmental changes; wherein the polymeric element has a laminate structure comprising: a first layer having discrete conductive filler particles dispersed within a polymeric matrix, and a second layer comprising only a polymeric matrix;
wherein the switch alters the sensor output by switching from the first electrical state to the second electrical state, wherein the sensor output alters the memory of the chip, and wherein the memory of the chip is configured to be read by an interrogator communicating with the first antenna of the tag.

5. The sensor system of claim 4 wherein the discrete conductive filler particles comprise particles selected from the group consisting of graphitized carbon powder and silver coated copper powder.

* * * * *